United States Patent [19]

Pleines et al.

[11] Patent Number: 4,696,297

[45] Date of Patent: Sep. 29, 1987

[54] PROCESS FOR COLLECTING FRAGMENTS WHICH ARE OBTAINED ON SHATTERING STONES IN BODY CAVITIES OF LIVING HUMANS AND OTHER MAMMALS

[75] Inventors: Peter Pleines, Cologne; Erich Wolf, Overath, both of Fed. Rep. of Germany

[73] Assignee: Farco-Pharma GmbH, Cologne, Fed. Rep. of Germany

[21] Appl. No.: 726,096

[22] Filed: Apr. 23, 1985

[30] Foreign Application Priority Data

Feb. 27, 1985 [DE] Fed. Rep. of Germany ....... 3506873

[51] Int. Cl.$^4$ .................. A61B 17/00; A61B 17/22
[52] U.S. Cl. ............................. 128/303.1; 128/319; 128/328
[58] Field of Search ............. 128/328, 303 R, 1 R, 128/319, 303.1, 399–401, 130

[56] References Cited

U.S. PATENT DOCUMENTS

| 4,196,736 | 4/1980 | Watanabe | 128/328 |
| 4,311,147 | 1/1982 | Hausler | 128/328 |
| 4,474,180 | 10/1984 | Angulo | 128/328 |
| 4,509,517 | 4/1985 | Zibelin | 128/328 |
| 4,589,415 | 5/1986 | Haaga | 128/328 |

Primary Examiner—Richard J. Apley
Assistant Examiner—H. Macey
Attorney, Agent, or Firm—Kontler Peter K.

[57] ABSTRACT

For collecting fragments obtained on crushing stones in body cavities of living humans or animals, a gelatin solution is introduced into the body cavity. The gelatin solution which is fluid at body temperature, is hardened during shattering of the stones by rinsing with a cooling fluid.

21 Claims, 5 Drawing Figures

PROCESS FOR COLLECTING FRAGMENTS WHICH ARE OBTAINED ON SHATTERING STONES IN BODY CAVITIES OF LIVING HUMANS AND OTHER MAMMALS

BACKGROUND OF THE INVENTION

The present invention relates to a system for collecting fragments obtained on crushing stones in the body cavities of living humans and other mammals.

It is known for the purpose of removing kidney stones to introduce from the outside an operating probe into the kidney cavity and to shatter the stone or stones located therein by means of tools passing through the probe into the cavity, to such an extent that the fragments pass through the probe and can be drawn off through the latter. However, during shattering fragments can pass into lateral branches of the kidney cavity and can be overlooked. These stone residues are then left behind in the kidney cavity and form crystal nuclei for new stones.

SUMMARY OF THE INVENTION

The object of the present invention is to so design a system of the aforementioned type that it is easy to avoid stone residues being left behind.

The invention is characterized by the use of a gelatin jelly as a gel, which is transparent and flowable at body temperature, preferably 37° C., and is transparent and solid at a working temperature of 5° to 20° C., and preferably 12° C., below body temperature.

The flowable gelatin solution (sol) is introduced into the body cavity so that the stones to be shattered are embedded therein. As a result of the cooling of the solution, a solid gel is formed, in which the stones are enclosed and the stones are then shattered. The fragments can then no longer escape from the gel, remain in the field of vision of the surgeon and can be reliably removed. The gel is then liquefied and the gelatin solution removed again.

The gelatin jelly must be hardened by cooling during the shattering of the stone. Cooling can be brought about by a cooling fluid continuously flowing around the gelatin jelly and which is supplied and removed again by means of the probe. As soon as this cooling is interrupted, the gelatin jelly can again assume body temperature and liquefies without any further action being necessary. As the body temperature is effective even in the outermost pockets of a body cavity, e.g. a kidney cavity, no solid residues can remain in the long run. Even if on sucking out the liquid gelatin jelly after removing the stone remnants, liquid gelatin jelly residues are left behind in the kidney cavity pockets, these are not prejudicial because they are flowable and are rinsed out naturally with the urine. Liquid residues of the gelatin jelly are also unharmful in other body cavities. If, during the shattering process or due to remaining residues, some of the gelatin jelly enters the blood vessels, it is very rapidly liquefied by the ambient temperature and is rinsed out without causing blockages or having other harmful effects.

The gelatin jelly which is fluid at body temperature is appropriately kept mixed ready for use in a disposable container, preferably a disposable or one-way syringe, and after heating to 37° to 40° C. in the body cavity is e.g. injected through a probe into the cavity.

The removal of kidney stones, the disposable container is preferably a syringe with a capacity of 10 cc. Thus, with an adequate tolerance, this constitutes a sufficient amount for filling a human kidney cavity. Larger disposable containers can be used when treating larger body cavities.

It is recommended that the body cavity only be filled sufficiently far with the gelatin gel to ensure that the stone or stones to be shattered are completely enveloped. A working area must be left free within the body cavity into which the cooling fluid, which for cooling the gelatin gel during stone shattering and during stone residue collection continuously flows through the probe and away again, can flow.

Particularly when treating stones in kidney cavities, it is appropriate to use a probe which can be inserted in the body so as to provide external access to the body cavity. Observation optics, tools and lines can be passed to the body cavity from the outside through this probe. The probe is equipped with a cooling fluid supply line leading to and issuing at the probe tip, as well as with a cooling fluid return line for the purpose of cooling the gelatin jelly. It is in many cases desirable for the gelatin jelly which has hardened through cooling not to be deposited on the probe tip because this could impair the handling of the tools and the optics at the probe tip and, as a result, feed and suction openings could become blocked. To prevent this, the outer parts of the probe tip can appropriately be thermally insulated with respect to the cooling fluid line. If this is not sufficient, the outer parts of the probe tip could be made heatable to body temperature.

What is done with the probe tip can also be done with a longer portion of the probe or with the entire probe in that the outer parts of the probe are thermally insulated with respect to the cooling fluid supply line and/or are made heatable to body temperature.

Work can be carried out in an advantageous manner if the stone which is to be shattered is located in a bubble or bag of solidified gelatin jelly formed by the cooling fluid. The fragments then remain within the bubble and can be easily removed. The bubble can easily be formed by spraying with cooling fluid a stone embedded in the flowable gelatin solution. The cooling fluid flows around the stone and moves the gelatin solution to the side, and the gelatin jelly which solidifies as a result of the cooling fluid forms the desired bubble which is filled with the cooling fluid and surrounds the stone. By appropriate temperature control of the individual parts in the vicinity of the probe tip, it is even possible to ensure that the edge of the bubble surrounds the front end of the probe and adheres thereto and that the probe tip with the shattering tools projects into the bubble free from gelatin jelly.

The invention also relates to a process for collecting fragments which are obtained on shattering stones in body cavities of living humans and animals. This process is characterized in that the gel is formed by a gelatin jelly which is flowable at body temperature and solid at working temperatures of 5° to 20° C., and preferably 12° C., below body temperature; that a gelatin solution is formed from the gelatin jelly by heating and is introduced into the body cavity, particularly a kidney cavity, preferably by injection; that the stones to be shattered are enveloped by the gelatin solution within the body cavity while a working area is still left free within the body cavity; that the gelatin solution in the body cavity is then hardened by cooling the gelatin jelly; that the stones held by the gelatin jelly are shattered and the fragments formed secured; that the stone fragments are then removed; that the gelatin jelly is cooled during the shattering of the stone or stones; that, by breaking off the cooling action, the gelatin jelly is again converted into a gelatin solution due to body temperature; and that the gelatin solution is then removed, preferably by suction.

Cooling and hardening of the gelatin jelly appropriately take place by means of a constantly maintained cooling fluid flow, preferably a cooling water flow, with the cooling water being supplied through a cooling fluid supply line to a probe and being removed from the latter through a cooling fluid return line. The tools for shattering the stones are preferably mounted on the probe. The cooling fluid, preferably an isotonic aqueous solution such as physiological common salt solution, Ringer's solution or the like appropriately has a temperature of 0° to 6° C.

A preferred gelatin gel comprises a gelatin with a strength of 100 to 350, and preferably 280 to 300, Bloom degrees and is mixed with 65 parts by weight of demineralized water per 100 parts by weight of gelatin jelly. The gelling temperature is then approximately 27° C.

A suitable gelatin is commercially available in the Federal Republic of Germany under the trade name Pharmagelatine 300 Bloom, 3.0 mm particle size and is marketed by Deutsche Gelatinefabriken Stoess and Co., D-6930 Eberbach/Baden. 20 to 60 parts by weight of such a gelatin are used and topped up with water to 100 parts by weight, i.e. using 80 to 40 parts by weight of water. The water is demineralized.

The fully mixed gelatin jelly is sterilized and, while in the flowable heated state, is introduced into the aforementioned disposable containers which are then sealed in a sterile manner. The gelatin jelly can also be sterilized in the final receptacle (one-way syringe). For infection into the body cavity, the gelatin jelly is made flowable by heating in the disposable container.

BRIEF DESCRIPTION OF THE DRAWINGS

The invention is described in greater detail hereinafter with reference to the attached drawings wherein.

DETAILED DESCRIPTION OF THE PREFERRED EMBODIMENTS

Figure 1:
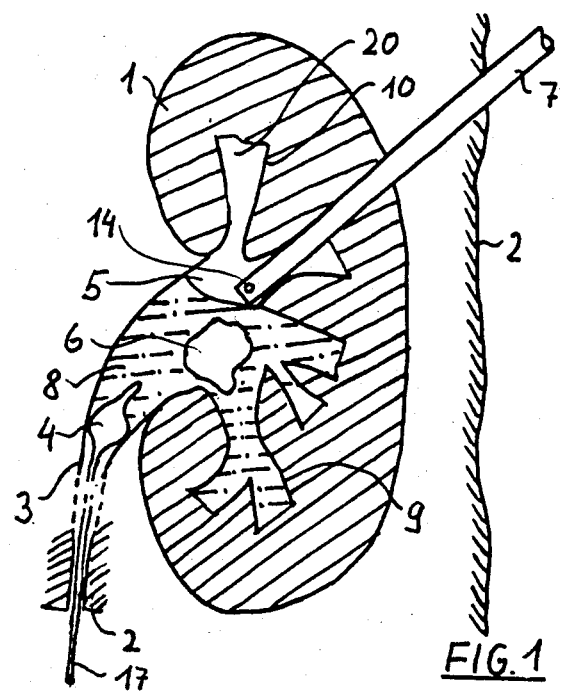
FIG. 1 is a section of a human kidney showing an insered probe and a stone surrounded by gelatin jelly.

In the drawing, 1 is the kidney tissue, 2 the body surface, 3 the ureter, 4 a balloon barrier or seal, 5 the kidney cavity, 6 a kidney stone, 7 a probe and 8 the solid gelatin jelly. The kidney cavity 5 branches into calices, e.g. kidney calices 9 and 10, and opens into ureter 3. Ureter 3 is tightly closed by means of the inflated balloon barrier 4 whose feed line 17 is so long that it passes through the entire ureter and out of the body. At the free projecting end of the feed line, the balloon barrier can be inflated or deflated in order to shrink it and pull it out.

Probe 7 has a continuous flow resectoscope shaft and is inserted in the body so that the tip reaches into the kidney cavity 5. Within probe 7 are provided a cooling fluid feed line 11 and a cooling fluid return line 12 which emanate from the rear end of the probe projecting from the body and have openings 13, 14 at the probe tip. Preferably, the probe is thermally insulated from the cooling fluid line in the vicinity of the tip by an insulating layer. A handle 18 (shown in FIG. 5) extends into the probe and is accessible from the rear end of the latter, the handle having a shattering tool, optics and a collecting device. These devices can be operated from the rear end of the probe and act on the probe tip. They can be extended into a working position, retracted and, optionally, interchanged. In addition, the probe has a pipe reaching into and out of the body cavity.

After closing the ureter by means of balloon barrier 4 and inserting the probe, the gelatin solution is introduced into the body cavity through the pipe in a quantity to ensure that a working area 20 remains free. The gelatin solution is then cooled by rinsing it with cooling fluid from the probe and is made to gel. Thus, the stone 6 is secured in the now solid gelatin jelly. Whilst the cooling fluid flow is maintained, tool 21 of probe 7 is extended as in FIG. 2 so that it contacts the stone 6 and shatters the latter to the extent that the fragments can be conveyed away through the probe via the aforementioned pipe. The fragments are held in situ by the solid gelatin jelly and can be reliably conveyed away. When this has taken place, the cooling fluid flow is stopped and rinsing takes place with warm water at 37° to 40° C. so that the gelatin jelly is liquefied and rinsed out. The probe can then be retracted and the balloon barrier deflated and drawn out. Any jelly residues are liquefied by body heat and flow out via the ureter.

Probe 7 is preferably made from metal and is provided at its front end with thermal insulation 15 in the form of an internal plastic sleeve. The thermal insulation of the probe ensures that the probe tip is not excessively cooled so that the gelatin jelly does not harden and stick to the probe tip. A heating means can be provided for this purpose in place of or in addition to the insulation.

Figure 2:
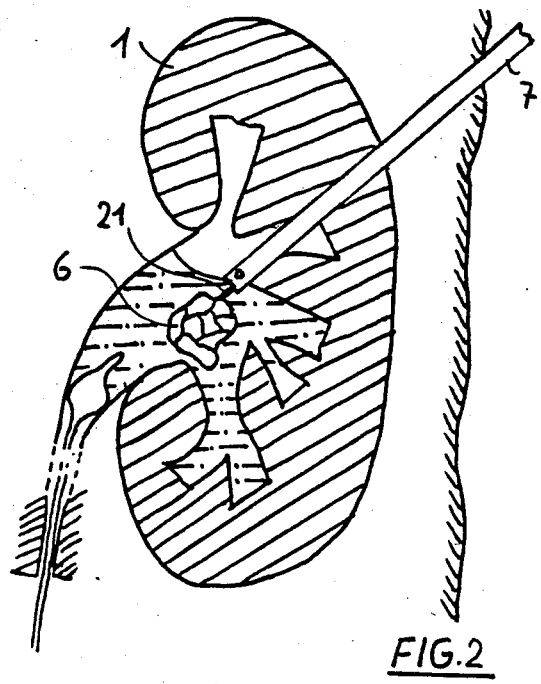
FIG. 2 is similar to FIG. 1 but with the probe shattering tool extended and the stone shattered.
Figure 3:
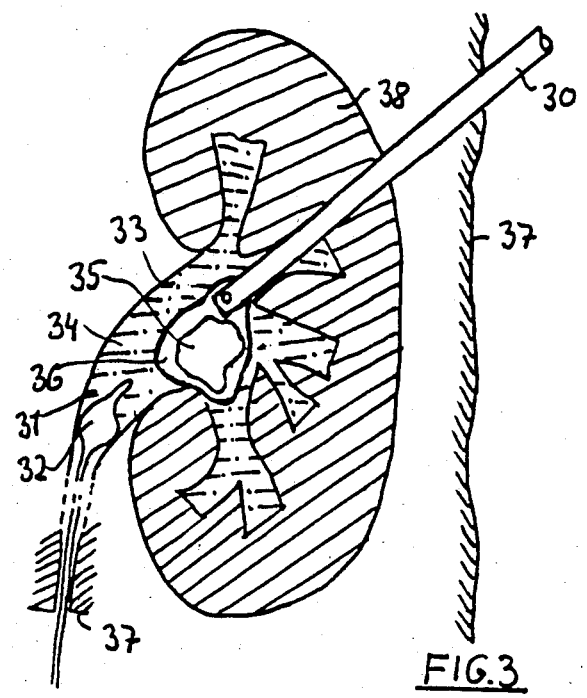
FIG. 3 is a section of a human kidney showing an inserted probe and a stone enveloped by a bubble or bag of gelatin jelly.
Figure 5:
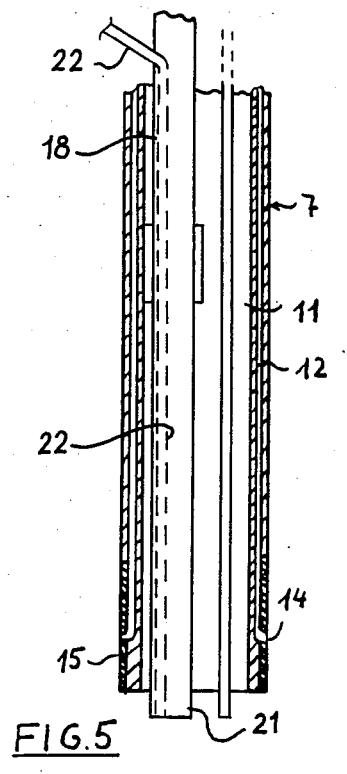
FIG. 5 shows the tip of the probe according to FIG. 1 in a partly sectional view.

FIG. 3 shows a probe 30 which has no thermal insulation but is otherwise constructed in the same way as the probe according to FIGS. 1, 2 and 5.

According to FIG. 3, after the ureter 31 has been closed by the balloon barrier 32 and probe 30 has been inserted so that the tip projects into the kidney cavity 33, the latter is partly filled with the gelatin solution 34. The cooling fluid flow is then started and is directed onto stone 35. The gelatin solution is forced away from the stone by the cooling fluid and, on hardening, forms a bubble or bag 36 which remains attached to the probe tip because this is also cooled by the cooling fluid. Stone 35 is located within this bubble 36 and can now be shattered and removed as described in connection with FIG. 2. The procedure is otherwise as described with reference to FIG. 2. In FIG. 3, 38 is the kidney tissue and 37 the body surface.

Figure 4:
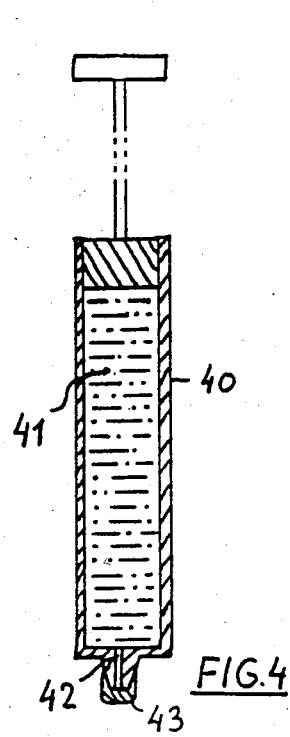
FIG. 4 shows a one-way syringe filled with gelatin jelly.

FIG. 4 shows a one-way syringe 40 which is filled with gelatin jelly 41. The outlet passage 42 is sealed in a sterile manner by a removable closure 43. The outlet passage 42 can be connected, at the rear end of the probe (not shown in FIG. 4), to a pipe 22 which passes through handle 18 and is open at the tip of the handle. The outlet passage 42 can then be introduced into the body cavity by means of the handle 18. For injection and removal, the contents of the syringe are heated to generate a flowable gelatin solution. On storing at ambient temperature, the contents of the syringe are in the form of a solid gelatin jelly.

What is claimed is:

1. A method of shattering a stone in a body cavity of a human or another mammal, comprising the steps of surrounding the stone with a substance in flowable state; transforming said substance to a non-flowable state so that at least the major part of the stone is confined by said substance; and shattering the stone while said substance is in said non-flowable state and confines the stone to thereby reduce scattering of the resulting stone fragments.

2. The method of claim 1, wherein the cavity is a kidney cavity.

3. The method of claim 1, said substance being flowable at body temperature; and wherein the transforming step comprises cooling said substance to below body temperature.

4. The method of claim 3, wherein the transforming step comprises cooling said substance about 5° to about 20° C. below body temperature.

5. The method of claim 4, wherein the transforming step comprises cooling said substance about 12° C. below body temperature.

6. The method of claim 1, wherein said substance is a gel in the non-flowable state thereof.

7. The method of claim 6, wherein said substance comprises gelatin.

8. The method of claim 1, wherein the surrounding step comprises injecting said substance into the cavity.

9. The method of claim 1, wherein the surrounding step comprises introducing said substance into the cavity in an amount such that said substance only partially fills the cavity.

10. The method of claim 1, further comprising the step of removing the stone fragments from the cavity.

11. The method of claim 1, further comprising the step of withdrawing said substance from the cavity subsequent to the shattering step.

12. The method of claim 11, further comprising the step of retransforming said substance to said flowable state subsequent to the shattering step; and wherein the withdrawing step is performed using suction.

13. The method of claim 1, wherein the transforming step comprises cooling said substance by contacting the latter with a cooling fluid.

14. The method of claim 13, wherein said cooling fluid is isotonic.

15. The method of claim 14, wherein said cooling fluid is an aqueous solution.

16. The method of claim 13, wherein said cooling fluid has a temperature of 0° to about 6° C.

17. The method of claim 1, wherein the transforming step comprises cooling said substance, said cooling being continued throughout at least the major part of the shattering step.

18. The method of claim 1, wherein the transforming step is performed in such a manner that a bubble of said substance is formed around the stone.

19. The method of claim 18, wherein the transforming step comprises cooling said substance by contacting the latter with a cooling fluid, said cooling fluid being directed onto the stone so that said substance is forced away from the stone to thereby form said bubble.

20. The method of claim 1, wherein the transforming step is performed in such a manner that the stone is embedded in a substantially continuous mass of said substance.

21. The method of claim 20, wherein the transforming step comprises cooling said substance by contacting the latter with a cooling fluid, said cooling fluid being circulated around said substance to thereby form said mass.

* * * * *